United States Patent [19]

Haskell et al.

[11] 4,090,923

[45] May 23, 1978

[54] BUTADIENE PURIFICATION WITH SIMULTANEOUS PREFRACTIONATION AND VINYLACETYLENE REJECTION

[75] Inventors: Donald M. Haskell, Bartlesville; Cecil O. Carter, Wann, both of Okla.

[73] Assignee: Phillips Petroleum Company, Bartlesville, Okla.

[21] Appl. No.: 785,157

[22] Filed: Apr. 6, 1977

[51] Int. Cl.² .............................................. B01D 3/40
[52] U.S. Cl. ........................................ 203/51; 203/62; 203/81
[58] Field of Search ...................... 203/51, 58, 62, 82, 203/98, 81; 260/681.5

[56] References Cited

U.S. PATENT DOCUMENTS

| | | | |
|---|---|---|---|
| 2,360,859 | 10/1944 | Evans et al. | 196/13 |
| 2,382,603 | 8/1945 | Buell | 202/42 |
| 3,242,227 | 3/1966 | Kroeper | 260/681.5 |
| 3,436,438 | 4/1969 | Takao et al. | 260/681.5 |
| 3,496,069 | 2/1970 | Tschopp et al. | 203/62 |
| 3,584,069 | 6/1971 | Rodgers | 203/58 |
| 3,769,217 | 10/1973 | Bannister et al. | 203/53 |
| 4,012,289 | 3/1977 | Haskell | 203/51 |
| 4,024,028 | 5/1977 | Haskell | 203/51 |

Primary Examiner—Hiram H. Bernstein

[57] ABSTRACT

A $C_4$-hydrocarbon feedstream containing butenes, butadiene, and vinylacetylene is subjected to a first extractive distillation with a selective solvent to remove butenes and a first portion of vinylacetylene as the extract; by the extraction with a minor quantity of methylethyl ketone in the selective solvent in this step, it has been found that a major portion of the vinylacetylene can be rejected, together with the butenes in the rich extract and that simultaneously the quantity of butadiene extracted could be considerably reduced; in a second extractive distillation the butadiene-rich raffinate of the first extractive distillation is further purified by extractive distillation using a mixture of sulfolane and methylethyl ketone as the solvent; after solvent stripping, the butadiene stream is finally purified in a fractionation step, wherein further vinylacetylene is removed.

4 Claims, 1 Drawing Figure

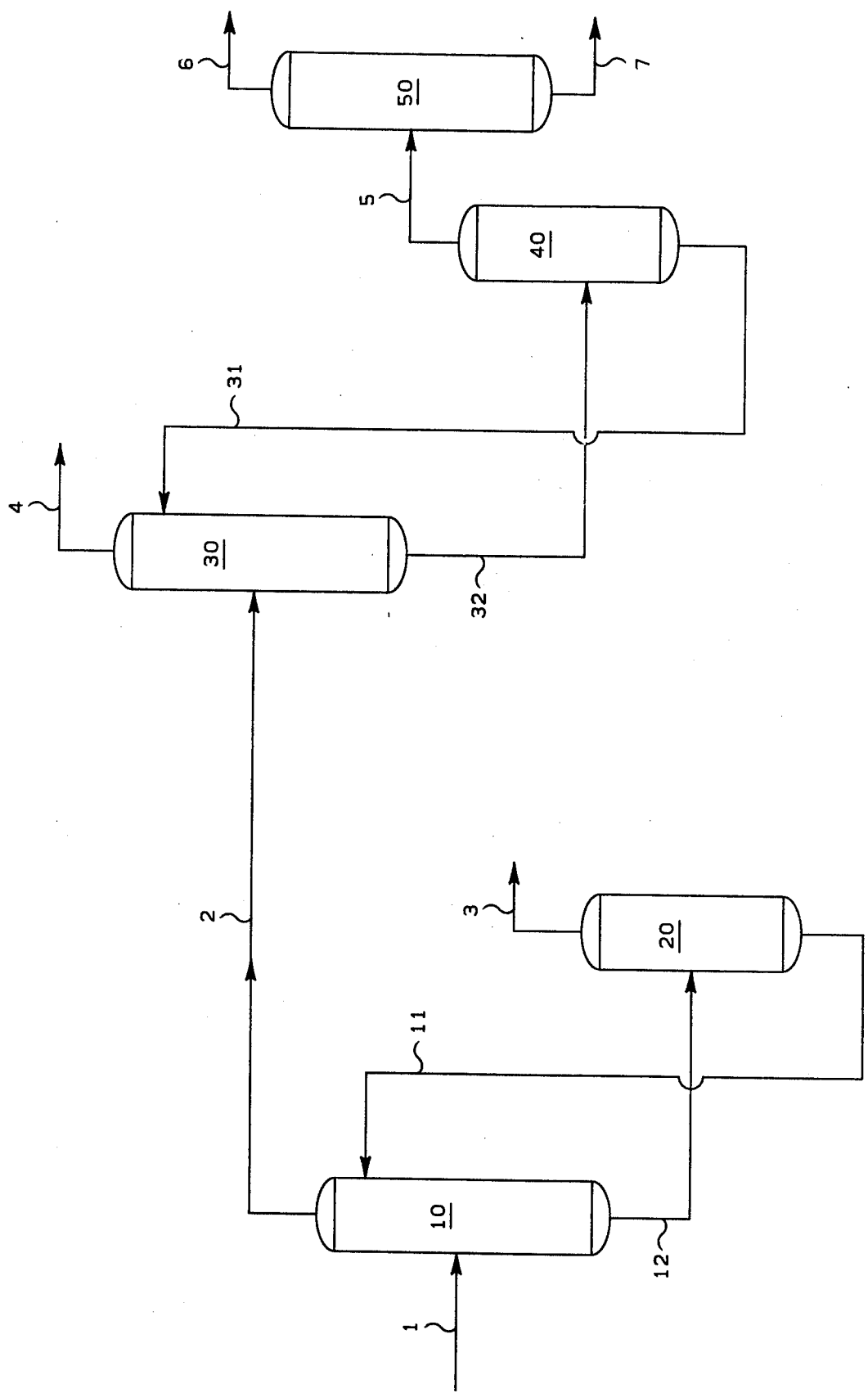

BUTADIENE PURIFICATION WITH SIMULTANEOUS PREFRACTIONATION AND VINYLACETYLENE REJECTION

The present invention relates to hydrocarbon separations. More specifically, the present invention relates to the removal of vinylacetylene from a butadiene stream. One aspect of the present invention is a process for purifying a butadiene-containing feed stream.

BACKGROUND OF THE INVENTION

Butadiene, in order to be useful as a monomer for the production of various polymers such as polybutadiene rubbers and other rubbery polymers, has to be essentially free of vinylacetylene. During the butadiene production, however, vinylacetylene to a certain degree is produced. $C_4$-concentrates from naphtha crackers, a major source of crude butadiene, contain a particularly high quantity of vinylacetylene.

In the recovery of butadiene from a mixed $C_4$-stream, this $C_4$-stream can be prefractionated to remove a portion of the relatively high boiling butene-2's and thereby enrich the butadiene overhead product which is subsequently processed by extractive and fractional distillation to remove butenes and vinylacetylene therefrom. The prefractionation just described can simultaneously reject a minor amount of vinylacetylene. Unfortunately this rejection can, however, not be carried out very far without losing an excessive quantity of butadiene. The final purification of butadiene for reducing the vinylacetylene content to, e.g., less than 50 ppm, is a considerable problem and expensive distillation columns with, e.g., 200 trays have to be used. This problem is aggravated by the fact that vinylacetylene when concentrated in a portion of a fractionator can spontaneously explode and cause large damage.

The Invention

It is one object of this invention to provide a process for purifying a mixed $C_4$-stream that contains butadiene.

Another object of this invention is to provide a process for removing efficiently and without undue butadiene losses, vinylacetylene from a feedstream containing butadiene and vinylacetylene.

A yet further object of this invention is to produce a purified butadiene stream from a feed stream containing only an absolutely small vinylacetylene concentration without the risk of concentrating vinylacetylene in any part of the equipment to a dangerous level.

These and other objects, advantages, details, embodiments and features of this invention will become apparent to those skilled in the art from the following detailed description of the invention, the appended claims, the examples and the drawing which shows a schematic flow diagram of a separation unit useful for carrying out the process of this invention. Unless otherwise noted, butadiene is used to describe 1,3-butadiene.

In accordance with this invention, a separation process is provided for wherein a $C_4$-feed stream consisting essentially of butadiene, butene-1, butene-2's, and vinylacetylene is subjected to a first extractive distillation with methylethyl ketone or a mixture of methylethyl ketone and sulfolane as the selective solvent such as to form a first raffinate stream which consists essentially of butadiene, butene-1, a smaller amount of butene-2's, and a smaller amount of vinylacetylene as compared to the feed stream, and a first rich solvent extract stream comprising the solvent, vinylacetylene and butenes-2. The first raffinate stream contains butene-2's and vinylacetylene in a weight ratio of at least 10:1. The first raffinate stream formed in this first extractive distillation is subjected to a second extractive distillation for separating the butene-1 utilizing a mixture of sulfolane and methylethyl ketone as the selective solvent. In this second extractive distillation, a second raffinate stream comprising butene-1, butene-2's, and some butadiene, and being essentially free of vinylacetylene, sulfolane and methylethyl ketone, as well as a second rich solvent extract stream consisting essentially of the selective solvent (sulfolane and methylethyl ketone), butadiene, a small amount of butene-2 and only a very minor amount of vinylacetylene are formed. The second rich solvent extract stream, too, contains butene-2 and vinylacetylene in a weight ratio of at least 10:1. The selective solvent is removed from the second rich solvent extract stream to form a solvent stream of sulfolane and methylethyl ketone and a stream of butadiene with some small quantity of vinylacetylene. This last mentioned stream is then subjected to a fractionation in which a relatively pure butadiene stream is produced and a stream of butene-2 and vinylacetylene. The concentration of vinylacetylene in this final fractionation never reaches a dangerous level in the fractionation zone.

Further embodiments of this invention comprise one or more of the specific features described in the following. Reference numerals in tables refer to the drawing.

The drawing shows a schematic flow diagram of the separation process of this invention. In the various distillation columns, only the essential flow streams have been shown and such details as reboilers and reflux units have been omitted. A mixed $C_4$-hydrocarbon feedstock, which preferably is a $C_4$-concentrate from a naphtha cracker is introduced into a first extractive distillation column 10 via line 1. Methylethyl ketone is introduced above the location of feedstock introduction into the distillation column 10 via line 11. A first raffinate stream having a reduced butene-2's and a reduced vinylacetylene content as compared to the feedstock, but containing nearly all the butadiene, namely generally at least 95% of the feedstock, is removed from the extractive distillation zone 10 via line 2. A first rich solvent extract stream comprising methylethyl ketone, butene-2's and vinylacetylene is withdrawn from the first extractive distillation column 10 via line 12.

The first rich solvent extract stream of line 12 is introduced into a first solvent stripper 20. From this solvent stripper an overhead stream is withdrawn via line 3 which overhead stream comprises butene-2's and vinylacetylene. A bottom stream consisting essentially of methylethyl ketone is withdrawn from the solvent stripper 20 and reintroduced via line 11 into the first extractive distillation column 10.

The first raffinate stream is introduced into a second extractive distillation column 30 via line 2. Above the point of introduction of this stream 2, a selective solvent stream consisting of sulfolane and methylethyl ketone is introduced into the second extractive distillation column 30 via line 31. A second raffinate stream comprising essentially all the butene-1 and some butene-2 is withdrawn from this extractive distillation column 30 via line 4. A second rich solvent extract stream consisting essentially of the solvent (sulfolane and methylethyl ketone), 1,3-butadiene, some butenes and the remaining small amount of vinylacetylene is withdrawn from the second extractive distillation column 30 via line 32. The second rich solvent extract stream from line 32 is introduced into a second solvent stripper 40 from which a butadiene stream consisting essentially of butadiene, butenes, and a small amount of vinylacetylene is withdrawn via line 5. The stripped solvent is reintroduced via line 31 into the second extractive distillation column 30. The butadiene stream 5 is fractionated to further reduce the concentration of butene-2 and vinylacetylene therein in a fractionator 50. The concentration of butene-2 and vinylacetylene is such that no dangerous concentration of vinylacetylene occurs within the fractionator 50. A purified butadiene stream is removed from the fractionator 50 via line 6, whereas a stream of butene-2 and vinylacetylene leaves the fractionator 50 via line 7.

One of the more specific problems solved by this invention is to avoid any explosion hazards caused, e.g., by spontaneous explosion of vinylacetylene during a process of removing vinylacetylene from a butadiene stream. Although the vinylacetylene concentrations are low in the regularly employed feed streams, much higher concentrations of vinylacetylene can occur in distillation columns. The explosion problem becomes particularly severe in situations where relatively high vinylacetylene concentrations are already present in the feedstock. Therefore, this invention is particularly applicable to such feedstocks containing relatively high amounts of vinylacetylene. A typical example of such a feedstock is $C_4$-concentrate from a naphtha cracking process.

The problem described is successfully solved by the process described in which a feedstock consisting essentially of butadiene, butene-1, butene-2, and vinylacetylene is subjected to two extractive distillations and a final fractionation as described.

More specifically, the feedstock compositions and the operating conditions for the process of this invention will be preferably within the ranges given in the following tables.

| Feedstock Compositions (parts by weight) of the $C_4$-Mixture | |
|---|---|
| | (stream 1) |
| 1,3-Butadiene | 30–60 |
| Butene-1 | 20–40 |
| trans Butene-2 | 15–30 |
| cis Butene-2 | 5–15 |
| Total butenes | 40–70 |
| Vinylacetylene | 0.5–3.0 |

These ranges are to be understood in the sense that the higher vinylacetylene concentrations occur in feedstocks with intermediate to higher butene concentrations.

| Operating Conditions for the First Extractive Distillation Column (column 10) | | | | |
|---|---|---|---|---|
| | MEK[1] Solvent | | 30 MEK/70 Sulfolane Solvent | |
| Feed temperature, °F (°C) | 80–125 | (29–52) | 80–125 | (27–52) |
| Reflux temperature, °F (°C) | 100–120 | (38–49) | 110–120 | (43–44) |
| Solvent temperature, °F (°C) | 90–125 | (32–52) | 90–125 | (32–52) |
| Solvent/Feed weight ratio | 0.4–2.3 | | 0.3–1.8 | |
| Reflux/Distillate weight ratio | 3–20 | | 2–20 | |
| Pressure, psig (MPa) | 60–100 | (0.52–0.79) | 60–100 | (0.52–0.79) |
| Kettle temperature, °F (°C) | 240–270 | (116–132) | 220–260 | (104–127) |

-continued

| Operating Conditions for the First Extractive Distillation Column (column 10) | | | | |
|---|---|---|---|---|
| | MEK[1] Solvent | | 30 MEK/70 Sulfolane Solvent | |
| °F (°C) | | | | |

[1]Methylethyl ketone.

The operation conditions for this second extractive distillation are given in the following table:

| Operating Conditions for Second Extractive Distillation Column (Ref. No. 30 in the drawing) | | |
|---|---|---|
| Feed temperature, °F (°C) | 80–130 | (27–54) |
| Reflux temperature, °F (°C) | 100–120 | (38–44) |
| Solvent temperature, °F (°C) | 120–160 | (49–71) |
| Solvent/Feed weight ratio | 4–8 | |
| Reflux/Distillate weight ratio | 2–15 | |
| Pressure, psig (MPa) | 80–100 | (0.65–0.79) |
| Kettle temperature, °F (°C) | 220–280 | (104–138) |

The $C_4$-raffinate that is extractively distilled under the operation conditions given above generally has a composition within the ranges shown in the following table:

| $C_4$-Raffinate Composition in Parts by Weight (stream 2 in the drawing) | |
|---|---|
| 1,3-Butadiene | 30–60 |
| Butene-1 | 20–46 |
| trans-Butene-2 | 5–15 |
| cis-Butene-2 | 0.2–0.6 |
| Total butenes | 25–60 |
| Vinylacetylene | 0.1–0.5 |

The weight ratio of butenes-2 to vinylacetylene in stream 2, the feed stream to the second extractive distillation column, should be at least 10:1.

The preferred weight range for the mixed solvent consisting of methylethyl ketone and sulfolane, both for the first and the second fractional distillation, is about 10 to about 40 wt. % methylethyl ketone and the rest sulfolane. Particularly, the mixed solvent comprising 30 wt. % methylethyl ketone and 70 wt. % sulfolane can be used.

Based on experimental results that will be given in the following examples, a material balance for the separation unit shown in the drawing has been calculated. This material balance illustrates the efficiency of the individual separation steps but does not illustrate the stream compositions to which this invention commercially is preferably applicable. The stream numbers in the following table which shows that material balance refer to the streams in the drawing. Operating conditions for the various columns are also shown.

| Stream No. | Material Balance (quantities in kg/hr) | | | | |
|---|---|---|---|---|---|
| | 1 | 2 | 3 | 4 | 5 |
| Methylacetylene | 0.01 | 0.01 | 0.0 | 0.01 | 0.0 |
| Vinylacetylene | 0.06 | 0.005 | 0.055 | 0.00 | 0.005 |
| Butene-1 | 26.86 | 26.73 | 0.13 | 25.97 | 0.76 |
| t-Butene-2 | 7.36 | 5.00 | 2.36 | 4.16 | 0.84 |
| c-Butene-2 | 4.07 | 0.15 | 3.92 | 0.07 | 0.08 |
| 1,3-Butadiene | 54.46 | 52.61 | 1.85 | 7.54 | 45.07 |

| | Operating Conditions | | | |
|---|---|---|---|---|
| Column No. | 10 | 20 | 30 | 40 |
| Feed Temp., | 122 (50) | 250 (127) | 125 (52) | 223 (106) |

-continued

| Column No. | Operating Conditions | | | |
|---|---|---|---|---|
| | 10 | 20 | 30 | 40 |
| °F (°C) | | | | |
| Reflux Temp., °F (°C) | 112 (44) | — | 116 (47) | — |
| Solvent Temp., °F (°C) | 94 (34) | — | 150 (66) | — |
| Solvent/Feed weight ratio | 1.0 | — | 7.0 | — |
| Reflux/Distillate weight ratio | 7.0 | — | 5.7 | — |
| Pressure, psig (MPa) | 70 (0.59) | 66 (0.56) | 88 (0.71) | 50 (0.45) |
| Kettle Temp., °F (°C) | 256 (124) | 297 (147) | 245 (118) | 315 (157) |

The particular advantages of this invention will become yet more apparent from the following example which is intended to further illustrate the invention but not to unduly limit the scope thereof. This example, too, illustrates the efficiency of individual steps but does not show the feed stream composition to which this invention is preferably applicable.

EXAMPLE

In a 4 inches (0.10 m) diameter distillation column having 140 sieve trays, a feedstock having the composition shown above in the material balance table as stream 1 was extractively distilled. The extract and raffinate was analyzed by gas chromatography and the percentage extracted was calculated from these results for the more important ingredients of the feedstock. The results of the rejection are shown in the following table; an optimized calculated run is also shown, the calculation being based on various actual runs and the mathematical method of regression analysis.

| Run No. | Results of Fractionations | | | | |
|---|---|---|---|---|---|
| | 1 | 2 | 3[(1)] | 4 | 5 |
| Solvent | None | MEK[(2)] | MEK | Furfural | 30 wt.% MEK 70 wt.% furfural |
| Reflux/Feed, wt. ratio | 6.04 | 6.5 | 5.2 | 6.29 | 6.4 |
| Solvent/Feed, wt. Ratio | 0.0 | 1.0 | 0.96 | 1.0 | 0.4 |
| Percent of Feed Component Extracted | | | | | |
| Vinylacetylene | 28.6 | 35.6 | 70.7 | 46.3 | 34.8 |
| Butene-1 | 4.4 | 0.2 | — | 0.1 | — |
| t-Butene-2 | 96.9 | 25.9 | 29.5 | 43.8 | 7.6 |
| c-Butene-2 | 100.0 | 96.6 | 91.1 | 68.6 | 13.7 |
| Butadiene | 10.7 | 1.1 | 1.6 | 2.4 | 8.4 |

[(1)]Optimum operation determined from several actual runs by regression analysis.
[(2)]Methylethyl ketone.

The results of the fractionations shown above show several important advantages of the present invention. The first run is a simple fractionation and resulted in removing only 28.6% of the vinylacetylene in the feedstock. The butadiene loss was an intolerable 10.7 wt. %. In the second run, the addition of only 1 part of methylethyl ketone per part of feedstock resulted in an increase in the vinylacetylene rejection to 35.6 wt. % while the butadiene loss was surprisingly lowered to the very small value of only 1.1 wt. %. By means of regression analysis, an optimized solution was obtained for Run 3. This regression analysis showed that it is possible to reject about 70 wt. % of vinylacetylene while losing only about 1.6 wt. % of butadiene and using a reflux to feed weight ratio of only 5.2 and a solvent to feed ratio of 0.96.

For comparison purposes, the fourth run was made extractively distilling the feedstock with furfural as the selective solvent. The vinylacetylene rejection was quite good in this run but the butadiene loss was roughly twice as high as in the case of methylethyl ketone. A 30:70 mixture of methylethyl ketone-furfural was tried in Run 5. It was surprisingly found that while the vinylacetylene rejection stayed in the same order of magnitude as in the case of methylethyl ketone, the butadiene rejection was increased to a very undesirable value of 8.4 wt. %.

A further important advantage of this invention lies in the feature that the vinylacetylene concentration is lowered in the butadiene containing feed stream in two steps; thus the absolute concentration of vinylacetylene in the stream by which this vinylacetylene is removed (streams 3 and 7 in the drawing) is low and kept well below the concentration where explosions can occur.

Reasonable variations and modifications which will become apparent to those skilled in the art can be made in this invention without departing from the spirit and scope thereof.

We claim:
1. A process for producing a purified butadiene stream comprising
   a. extractively distilling in a first extractive distillation zone a feed stream consisting essentially of butadiene, butene-1, butene-2's, and vinylacetylene with a selective solvent selected from the group consisting of a methylethyl ketone and methylethyl ketone/sulfolane mixtures to form a first raffinate stream consisting essentially of butadiene, butene-1, a smaller concentration of butene-2's and a smaller concentration of vinylacetylene than the feed stream and being essentially free of solvent, the weight ratio of the butene-2's to the vinylacetylene being at least 10:1, and a first rich solvent extract stream,
   b. stripping said first rich solvent extract stream in a first stripping zone to form a first solvent stream and a vinylacetylene stream,
   c. reintroducing at least a portion of said first solvent stream into said first extractive distillation zone as selective solvent,
   d. extractively distilling said first raffinate stream in a second extractive distillation zone using as the selective solvent a mixture of methylethyl ketone and sulfolane, the methylethyl ketone concentration in the mixture being about 10 to about 40 wt. % methylethyl ketone, to form a second raffinate stream, and a second rich solvent extract stream consisting essentially of the selective solvent, butadiene, butenes, and vinylacetylene, e. stripping said second rich solvent extract stream in a second stripping zone to form a second solvent stream consisting essentially of sulfolane and methylethyl ketone and a butadiene stream consisting essentially of butadiene, butenes and vinylacetylene, f. recycling at least a portion of said second solvent stream to said second extractive distillation zone as selective solvent, g. fractionally distilling said butadiene stream to form a purified butadiene stream and a butenes and vinylacetylene-comprising stream, and h. recovering said purified butadiene stream as the product of the process.

2. A process in accordance with claim 1 wherein said feed stream has the following composition in parts by weight:

| | |
|---|---|
| 1,3-Butadiene | 30–60 |
| Butene-1 | 20–40 |
| trans Butene-2 | 15–30 |
| cis Butene-2 | 5–15 |
| Total butenes | 40–70 |
| Vinylacetylene | 0.5–3.0 |

3. A process in accordance with claim 1 wherein said feed stream is a $C_4$-concentrate from a naphtha cracking process.

4. A process in accordance with claim 1 wherein said selective solvent of step (a) is methylethyl ketone and the solvent/feed ratio in the extractive distillation of step (a) is about 1.

* * * * *